United States Patent [19]

Barberet et al.

[11] Patent Number: Plant 5,513

[45] Date of Patent: Jul. 16, 1985

[54] CARNATION NAMED LONBIRA

[75] Inventors: Nicole Barberet; Yves Ducloux, both of Antibes, France

[73] Assignee: Laboratoire de Physiologie Vegetale de la Londe, La Londe, France

[21] Appl. No.: 516,511

[22] Filed: Jul. 25, 1983

[51] Int. Cl.[3] ..... A01H 5/00
[52] U.S. Cl. ..... Plt./70
[58] Field of Search ..... Plt./70

*Primary Examiner*—Robert E. Bagwill

*Attorney, Agent, or Firm*—Chas. W. Rummler

[57] ABSTRACT

A new carnation plant particularly distinguished by its general tangerine-orange coloration with cherry colored streaks in a generally dome-shaped form of medium size, the blooms being produced profusely during the recurrent blooming seasons of this plant and borne singly on straight stems of medium length. This plant has a tall, vigorous and upright growth habit with an abundant quantity of foliage and an apparent resistance to Fusarium Oxysporum.

1 Drawing Figure

BACKGROUND OF THE NEW PLANT

This new carnation plant was discovered by us in 1977 as a sport of the carnation variety "Londorga" (unpatented) growing among our collection of carnation plants maintained at La Londe, Les Maures, France, for the purpose of producing improved carnation plants for the commercial market. The beautiful orange coloration of this mutation of "Londorga" led us to propagate it, by means of cuttings, to test its growth characteristics and flower production and the favorable characteristics of the plant so produced caused us to continue its propagation through several successive generations at La Londe, We thereby determined that we had a new carnation variety having very strong and advantageous growth characteristics and excellent production of blooms such as to make it a very valuable development for the production of carnation flowers for the cut flower market. The propagation of this new plant through many generations since its discovery has also demonstrated that the novel characteristics of blossom color and plant growth habit hold true from generation to generation and appear to be firmly fixed.

DESCRIPTION OF THE DRAWING

Our new variety of tangerine-orange carnation plant is illustrated by the accompanying photographic drawing which has been hand painted, in part, to show the form and color characteristics of the flowers, the color rendition being as nearly true to the several colors specified as it is reasonably possible for the artist to apply to a bloom of such color variegation.

DESCRIPTION OF THE NEW PLANT

The following is a detailed description of our new carnation plant based upon observations of greenhouse grown plants made at La Londe, France, in the Spring of 1983, the color designations being according to The R.H.S. Colour Chart of The Royal Horticultural Society at London, England.

THE PLANT

Origin: Mutation.
Parentage: "Londorga" (unpatented).
Classification:

*Botanic.*—*Dianthus caryophyllus.*
*Commercial.*—Standard Carnation.
Form: Tall, leafy bush.
Height: About 125 cm. at six months.
Growth: Vigorous, upright, rapid and rigid.
Main stem:
*Length.*—Less than 15 cm. due to pinching.
Branching character: This plant is rather well branched with at least four stems being emitted from near the ground.
Foliage:
*Quantity.*—Abundant.
*Number of leaves.*—More than 120.
*Size of leaf.*—About 15 cm. long and 1.5 cm. wide, in average at the seventh node.
*Leaf shape.*—Linear with rolled margins.
*Texture.*—Leathery.
*Color.*—Upper side — 189B. Under side — 189B.
*Ribs and veins.*—Hardly noticeable.
*Rachis.*—Hardly noticeable.

THE BUD

Size: Medium.
*Diameter.*—About 2 cm in average.
*Length.*—About 3.7 cm. in average.
Shape: Ovoid and nearly cylindrical.
Opening rate: Normal for carnations.
Color of petals:
*When sepals first divide.*—23C. and 46D.
*When petals begin to unfurl.*—23C and 24B.
Sepals:
*Number.*—Five.
*Shape.*—Joined at the lower part with the upper portion of generally ovate character and having a sharp pointed apex.
*Character.*—The sepals are hooded over the bud and curl back when the flowers open.
*Color.*—Inside — Greenish White. Outside — 137D and 145B.
*Striae.*—Longitudinal.
Calyx:
*Shape.*—Almost cylindrical widening toward the top.
*Size.*—Medium.
*Splitting.*—Sometimes the calyx splits.
*Aspect.*—Smooth.

Flower stem:
*Length.*—About 65 cm.
*Character.*—Erect and rigid.
*Color.*—145C and 189B.

THE FLOWER

Blooming habit: Recurrent, blooming profusely in the Spring and Fall seasons.
Size of bloom: Medium.
*Diameter.*—About 9 cm. in average.
*Depth.*—About 6.2 cm. in average.
Borne: Singly on rigid, upright stems.
Shape: When bloom first opens, high centered. When bloom matures, dome shaped.
Petalage:
*Number.*—Averaging about 50.
*Arrangement.*—Imbricated.
*Form.*—Fan shaped with an apex that is more smooth than serrated.
*Texture.*—Soft.
*Appearance.*—Satiny.
*Color.*—Outer Petal: Body —24B, 25C and 45C. Base — Yellowish Green. Reverse side — 23C and 46D. Inside Petal: Body — 24B, 25C and 45C. Base — Yellowish Green. Reverse side — 23C and 46D.
Petaloids: Petaloids are rare and when existing are smaller than petals.
*Color.*—The same as the petals.
Flower stem:
*Length.*—About 65 cm., cut at the tenth node.
*Character.*—Of good strength and upright habit.
*Color.*—145C and 189B.

Fragrance: Fragrance is present.
Persistence: The petals hang on and dry.
Lasting quality:
*As cut flower.*—At least ten days in vase keeping.
Disease resistance: Resistance to *Fusarium oxysporum* as observed INRA, Antibes, Alpes-Maritimes, France.

REPRODUCTIVE ORGANS

Stamens:
*Number.*—Average about 15.
*Arrangement.*—Around the pistils.
*Anthers.*—Size: Less than 4 mm. Color: Whitish.
*Filaments.*—Color — Whitish.
Pistils:
*Number.*—2 to 4.
*Styles.*—Color — Greenish White.
*Stigmas.*—Color — Lightly Pinkish.
Character of ovaries: The ovaries are ribbed.

The growth habit of this new plant is similar to that of its parent "Londorga". Its color can be compared to that of "Tangerine" (U.S. Plant Pat. No. 1,734); however, the color of this new plant is a brighter orange than that of "Tangerine".

We claim:

1. A new and distinct variety of carnation plant, substantially as herein shown and described, characterized by its abundant production of medium sized flowers of a generally tangerine-orange coloration during each of its recurrent blooming seasons, and its tall, rapid and erect growth habit with an abundant production of foliage.

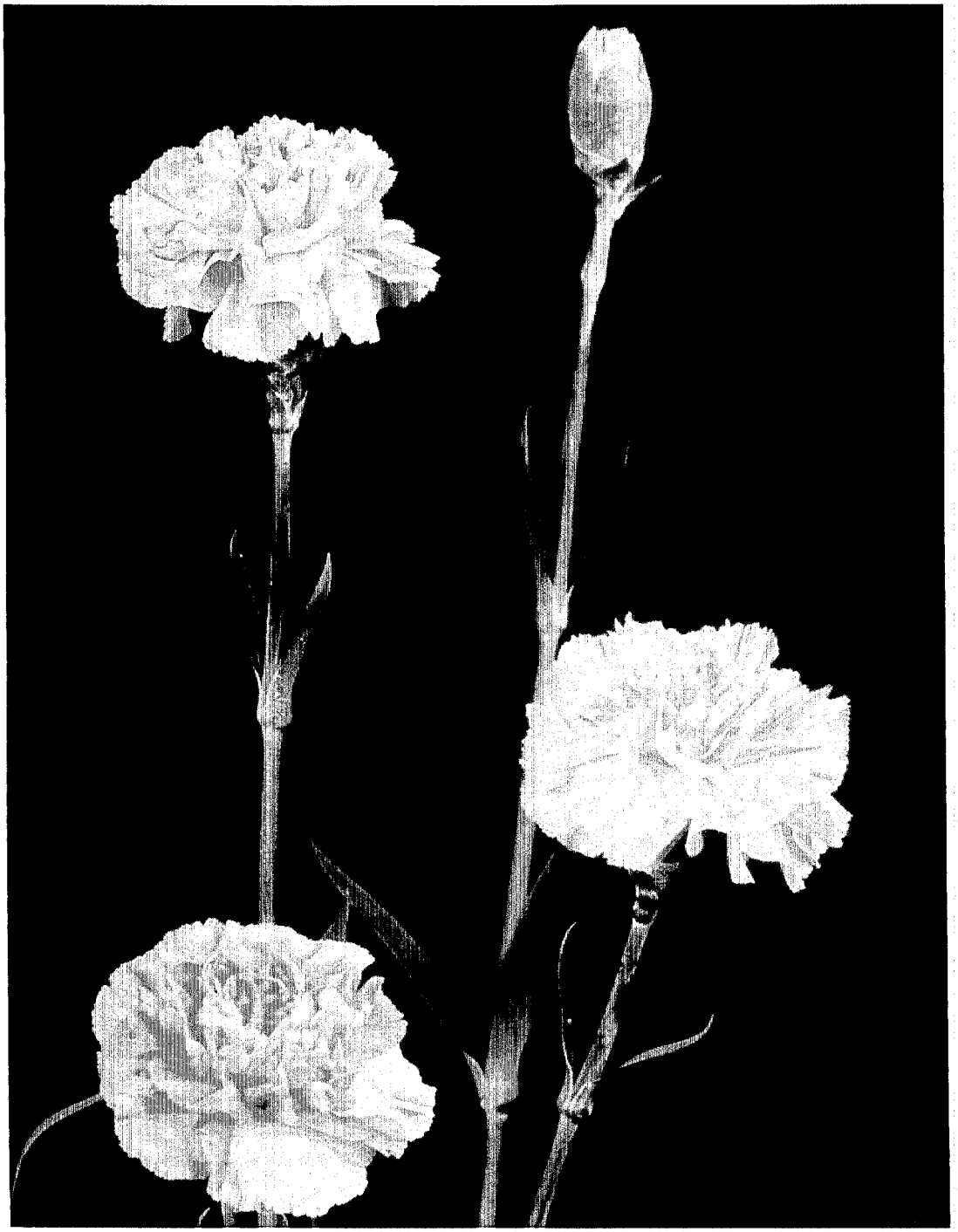

* * * * *